United States Patent
Ono et al.

[11] Patent Number: 5,755,669
[45] Date of Patent: May 26, 1998

[54] BLOOD PRESSURE MONITORING APPARATUS

[75] Inventors: Kohei Ono; Hiromitsu Kasuya; Yoshihiro Sugo; Takeshi Sohma; Wenxi Chen, all of Tokyo, Japan

[73] Assignee: Nihon Kohden Corporation, Tokyo, Japan

[21] Appl. No.: 841,684

[22] Filed: Apr. 30, 1997

[51] Int. Cl.$^6$ ................................................ A61B 5/00
[52] U.S. Cl. ............................ 600/494; 600/495; 600/500
[58] Field of Search ........................... 600/485, 493–496, 600/500

[56] References Cited

U.S. PATENT DOCUMENTS

| | | | |
|---|---|---|---|
| 4,807,596 | 2/1989 | Schmid et al. | 600/500 |
| 4,907,638 | 3/1990 | Sramek | 600/485 |
| 5,033,472 | 7/1991 | Sato et al. | 128/691 |
| 5,199,438 | 4/1993 | Pearlman | 128/670 |
| 5,237,997 | 8/1993 | Greubel et al. | 600/500 |
| 5,339,822 | 8/1994 | Taylor et al. | 128/700 |
| 5,564,427 | 10/1996 | Aso et al. | 128/681 |
| 5,603,329 | 2/1997 | Hosaka et al. | 600/494 |
| 5,649,543 | 7/1997 | Hosaka et al. | 600/494 |

FOREIGN PATENT DOCUMENTS

| | | | |
|---|---|---|---|
| 0 498 281 | 8/1992 | European Pat. Off. | A61B 5/0285 |
| 0 698 370 | 2/1996 | European Pat. Off. | A61B 5/0225 |

*Primary Examiner*—Robert L. Nasser
*Attorney, Agent, or Firm*—Sughrue, Mion, Zinn, Macpeak & Seas, PLLC

[57] ABSTRACT

After an initial blood pressure measurement using a cuff 2 has been made, not only a pulse wave propagation time Tt is counted consecutively, but also a pulse wave propagation time change ΔT is calculated every time the pulse wave propagation time Tt is counted and compared with a pulse wave propagation change threshold ΔTs. When the pulse wave propagation time change ΔT exceeds the pulse wave propagation time change threshold ΔTs, not only a blood pressure value BPt is measured with the cuff 2, but also a pulse wave propagation time $Tt_1$ is counted. If there are at least two sets of data, each set of data consisting of a blood pressure value BPt and a pulse wave propagation time $Tt_1$, coefficients α, β specific to a subject are calculated from such two sets of data by a least-squares method. Then, the pulse wave propagation time change threshold ΔTs is calculated from the coefficient α, and the current pulse wave propagation time change threshold ΔTs is updated.

3 Claims, 5 Drawing Sheets

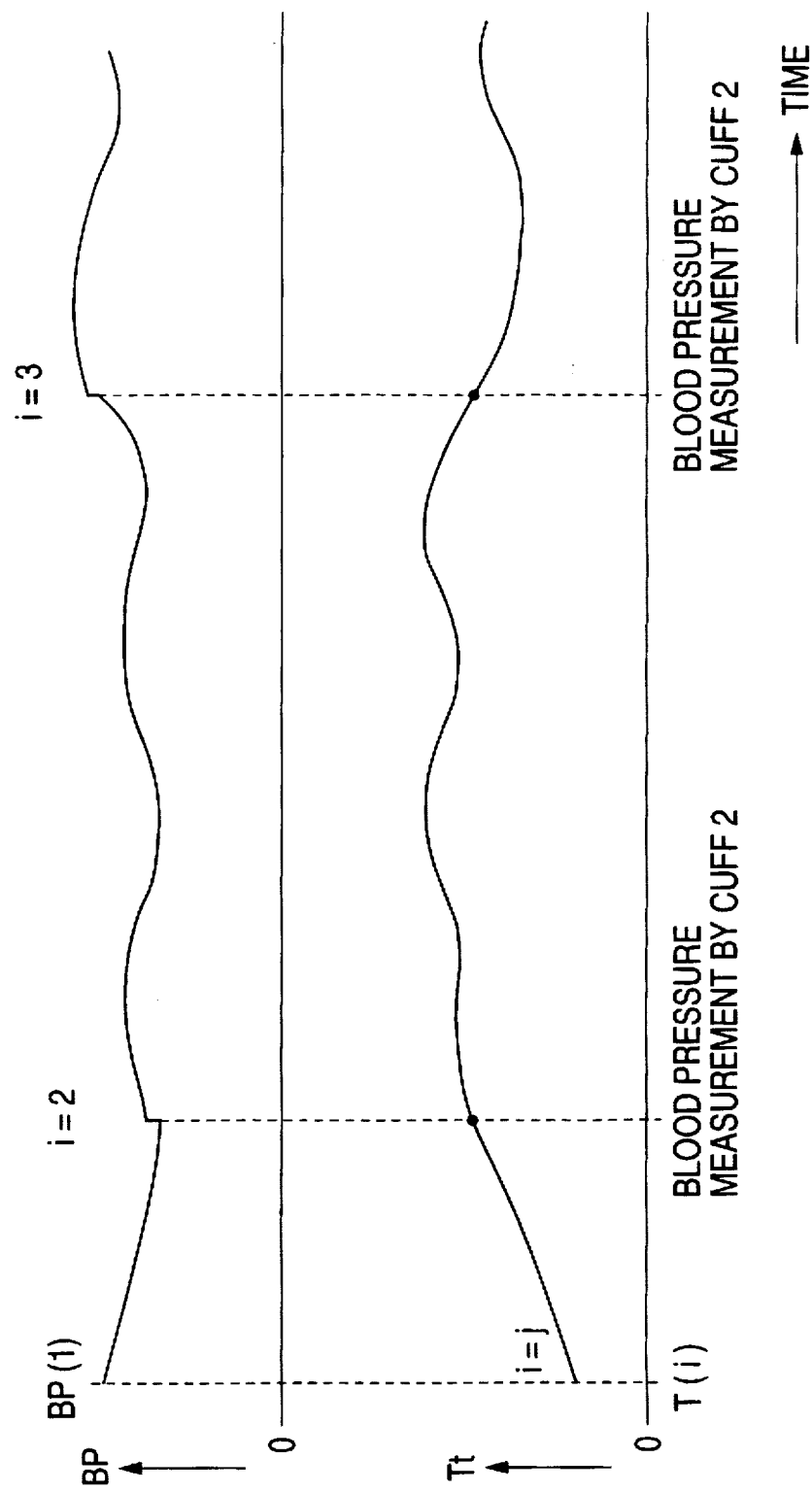

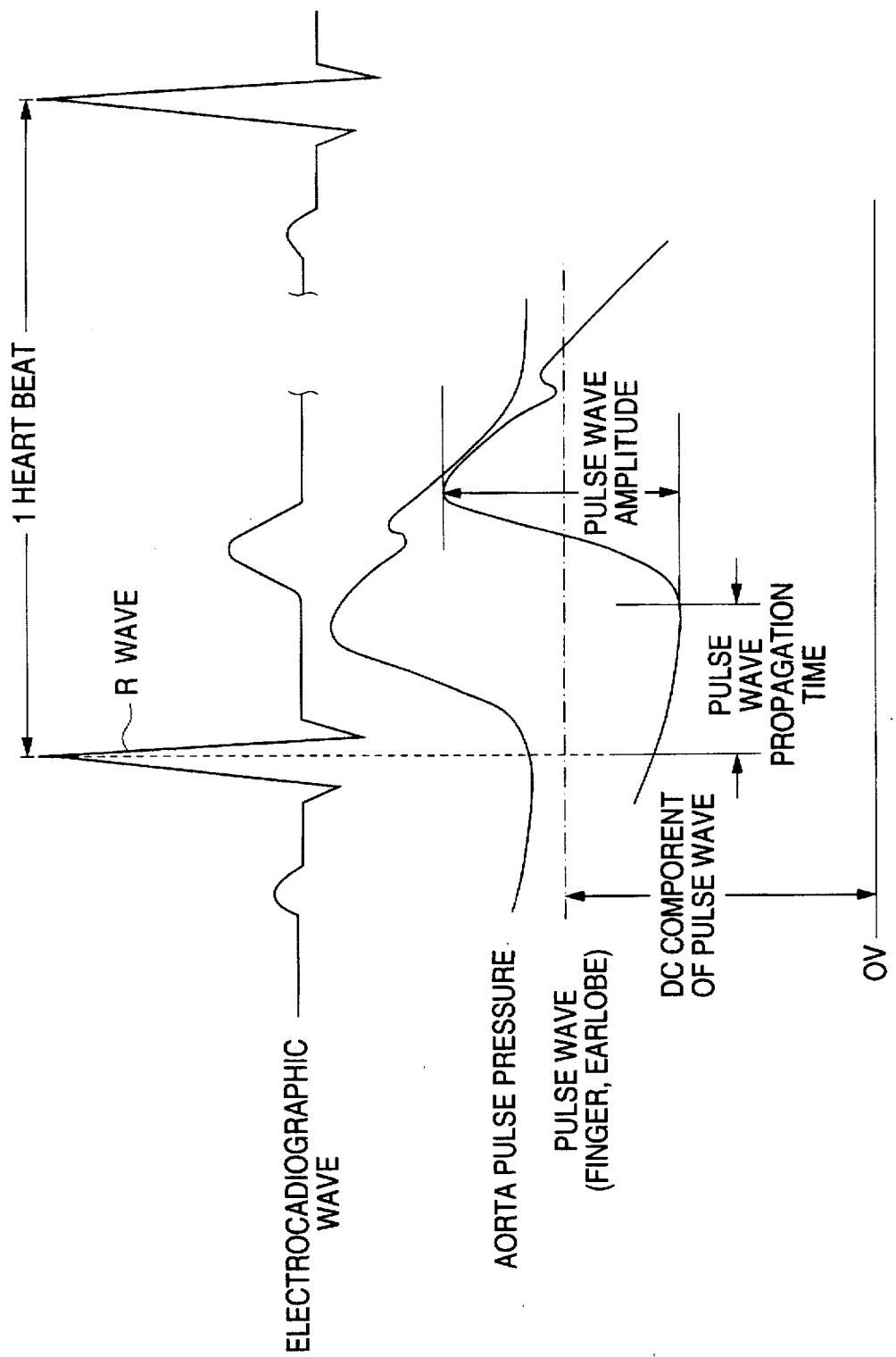

BLOOD PRESSURE MONITORING APPARATUS

BACKGROUND OF THE INVENTION

1. Field of the Invention

The present invention relates to blood pressure monitoring apparatuses to be applied to such fields as requiring continuous blood pressure monitoring for subjects to be treated in operating rooms, intensive care units, a first-aid rooms, an extracorporeal dialysis rooms, and the like. More particularly, the present invention is directed to a blood pressure monitoring apparatus that monitors blood pressure by means of pulse wave propagation time.

2. Related Art

Available as a blood pressure monitoring apparatus that monitors blood pressure by continuously measuring the blood pressure of a subject are a noninvasive blood pressure measurement type based on an oscillometric method by wrapping a cuff around the brachium of a subject and an invasive blood pressure measurement type that involves insertion of a needle into an artery of a subject. Further, blood pressure measurement based on pulse wave propagation velocity is also available as the noninvasive blood pressure measurement type.

By the way, conventional blood pressure monitoring apparatuses have addressed the following problems.

(1) In a blood pressure monitoring apparatus that measures blood pressure in a noninvasive manner using a cuff, the problem arises when blood pressure is measured periodically at a long time interval. That is, a sudden turn for the worse such as a shock in blood pressure has, in some cases, been missed when the blood pressure is measured at a time interval exceeding 5 minutes, for example. It may be noted that by shortening the measuring cycle to, e.g., 1 minute, the likelihood of missing sudden changes in blood pressure can be reduced. However, when the measuring cycle is shortened, the blood vessel of a body part around which the cuff is wrapped is burdened.

(2) Further, when blood pressure is measured periodically, the subject is burdened with the part of his or her body being pressured with the cuff more frequently than necessary.

(3) In a blood pressure monitoring apparatus of the invasive measurement type, the subject may, in some cases, be mentally burdened by stress, or be introduced the risk of infection, bleeding and the arterial occlusion. Further, such blood pressure monitoring apparatus entails more cumbersome operation than a blood pressure monitoring apparatus of the noninvasive blood pressure measurement type, which in turn burdens the medical staff as well.

(4) Blood pressure measurements based on pulse wave propagation velocity are not sufficiently accurate.

SUMMARY OF THE INVENTION

Therefore, the object of the present invention is to provide a blood pressure monitoring apparatus that can monitor blood pressure continuously, safely, and highly accurately without giving burdens to a subject.

According to an aspect of the present invention, there is provided a blood pressure monitoring apparatus that includes: blood pressure measuring means for measuring blood pressure using a cuff; blood pressure value storage means for storing a blood pressure value measured by the blood pressure measuring means; threshold storage means for storing a pulse wave propagation time change threshold and a blood pressure change threshold that are inputted from an external source; time interval detection reference point detecting means for detecting a time interval detection reference point on a pulse wave at an aorta of a body; pulse wave detecting means for detecting a pulse wave at a peripheral blood vessel appearing with a time delay with respect to the pulse wave at the aorta; pulse wave propagation time counting means for counting a pulse wave propagation time based on detected outputs from the time interval detection reference point detecting means and the pulse wave detecting means; pulse wave propagation time storage means for storing a pulse wave propagation time counted by the pulse wave propagation time counting means when the blood pressure has been measured by the blood pressure measuring means; first logic operation means for calculating a pulse wave propagation time change from two pulse wave propagation times counted by the pulse wave propagation time counting means; second logic operation means for calculating coefficients specific to a subject from at least two blood pressure values stored in the blood pressure value storage means and from the pulse wave propagation times stored in the pulse wave propagation time storage means corresponding to the each blood pressure values, the coefficients allowing equations expressing a relationship between blood pressure and pulse wave propagation time to be established; third logic operation means for updating a pulse wave propagation time change threshold stored in the threshold storage means by dividing a blood pressure change threshold read from the threshold storage means by a calculated coefficient specific to the subject; judgement means for judging whether or not the calculated pulse wave propagation time change exceeds the pulse wave propagation time change threshold read from the threshold storage means; and control means for measuring blood pressure of the subject using the cuff by controlling the blood pressure measuring means and controlling the pulse wave propagation time change threshold updating operation when it is judged that the pulse wave propagation time change exceeds the pulse wave propagation time change threshold.

Further, according to another aspect of the present invention, the second logic operation means calculates the coefficients specific to the subject by a least-squares method using at least two blood pressure values stored in the blood pressure value storage means and the pulse wave propagation times stored in the pulse wave propagation time storage means corresponding to the each blood pressure values, the coefficients being equivalent to a single regression coefficient and a coefficient term when the relationship between blood pressure and pulse wave propagation time is expressed in the form of a single regression line.

BRIEF DESCRIPTION OF THE DRAWINGS

FIG. 4 is a waveform diagram illustrative of an operation of the blood pressure monitoring apparatus shown in FIG. 1.

FIG. 5 is a waveform diagram illustrative of a pulse wave propagation time.

DETAILED DESCRIPTION OF THE PREFERRED EMBODIMENTS

Figure 1:
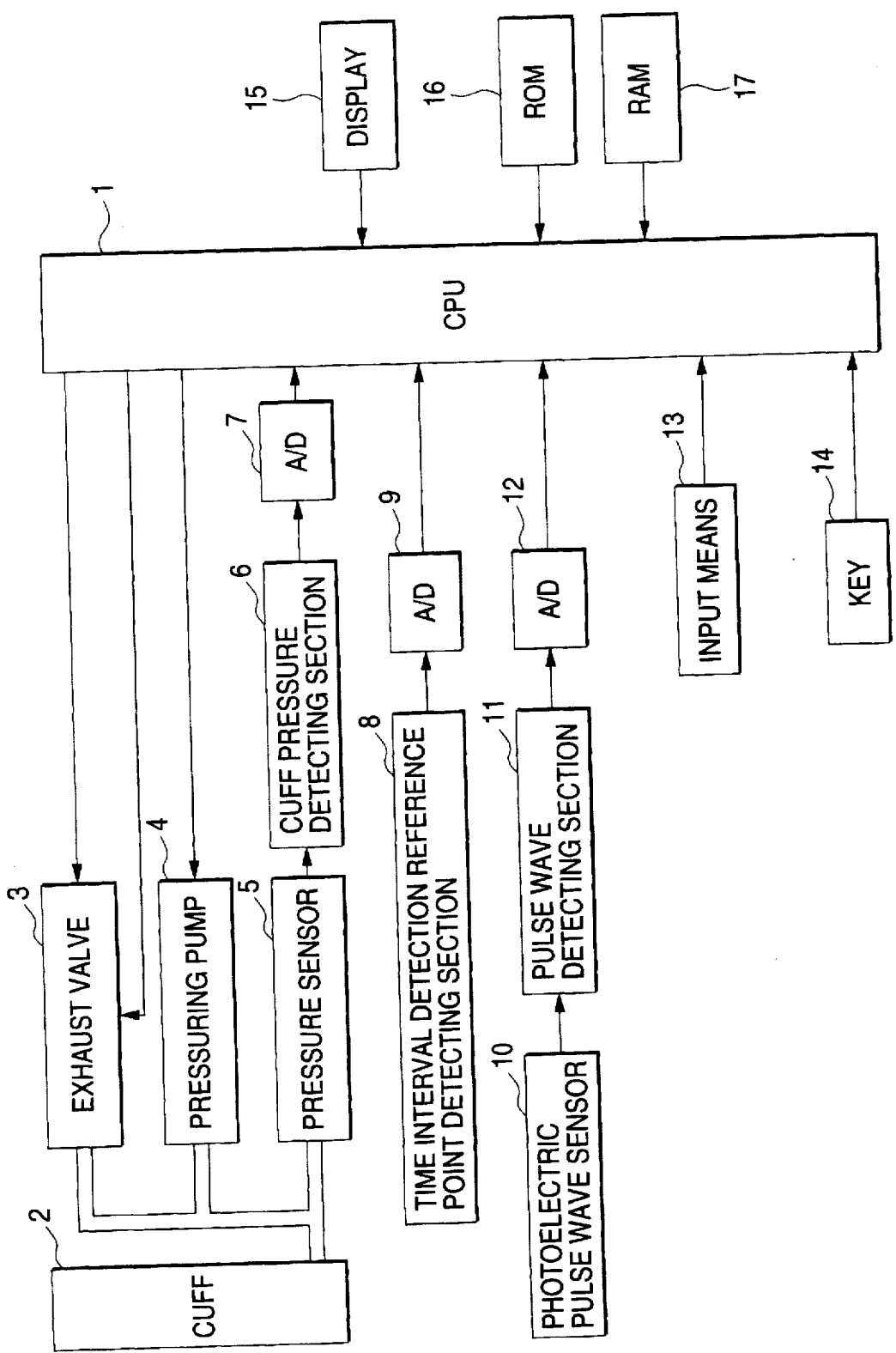
FIG. 1 is a block diagram showing a configuration of a blood pressure monitoring apparatus, which is a first embodiment of the present invention.

The first basic concept of the present invention will hereunder be described.

The principle of a blood pressure measuring method based on pulse wave propagation velocity is as follows.

As shown in FIG. 5, the specific point of a pulse wave on the side of a peripheral blood vessel such as a finger or a ear appears with a delay with respect to the specific point of an aortic pulse wave. This delay time is the pulse wave propagation time.

A pulse wave propagation velocity corresponding to a pulse wave propagation time at a predetermined distance appears as a function of the volume elasticity of a blood vessel. The volume elasticity of a blood vessel increases with increasing blood pressure, and the blood vessel wall becomes hard, which in turn increases propagation velocity. Therefore, a blood pressure change can be detected from the pulse wave propagation velocity.

A sphygmomanometer using this pulse wave propagation time must be calibrated by measuring blood pressure through other means, e.g., using a cuff, and referring to the measured results.

Such calibration requires measurements of both blood pressure values and pulse wave propagation times when a subject is, e.g., at rest and in exercise.

Here, assuming that the blood pressure value and the pulse wave propagation time at the time the subject is at rest are P1, T1 and that those at the time the subject is in exercise are P2, T2, and further assuming that coefficients specific to the subject are $\alpha$, $\beta$, then the blood pressure values P1, P2 are given as follows.

$$P1 = \alpha T1 + \beta$$

$$P2 = \alpha T2 + \beta$$

Therefore, by measuring P1, T1, P2, T2, $\alpha$, $\beta$ can be calculated from the above two equations. Once $\alpha$, $\beta$ have been calculated, the blood pressure values of the subject can thereafter be measured only by measuring the pulse wave propagation time. It may be noted that in measuring two different blood pressure values, the measuring timings are not limited to such timings at which the subject is at rest and in exercise as long as measuring timings are such as to allow two different blood pressure values to be picked up when different blood pressures appear.

Blood pressure fluctuations of a subject can be monitored by consecutively measuring the pulse wave propagation time. In this case, when the pulse wave propagation time change $\Delta T$ exceeds a preset pulse wave propagation time change threshold $\Delta Ts$, it is judged that a sudden change has occurred in the blood pressure fluctuation of a subject, and a blood pressure measurement is made using the cuff at this moment. Further, in this case, noise may be picked up in the measured values that are to be used for calculating $\alpha$, $\beta$ or $\alpha$, $\beta$ may thereafter fluctuate. Therefore, $\alpha$, $\beta$ are calculated again when the pulse wave propagation time change $\Delta T$ exceeds the pulse wave propagation time change threshold $\Delta Ts$. Further, the pulse wave propagation time change threshold $\Delta Ts$ is calculated based on the calculated value $\alpha$ to update the current pulse wave propagation time change threshold $\Delta Ts$.

The above operation prevents the subject from being burdened as in the case where blood pressure measurements are continuously made using the cuff at a predetermined cycle, which in turn contributes to significantly reducing burdens given to the subject and allowing blood pressure fluctuations to be monitored with high accuracy.

A blood pressure monitoring apparatus, which is a first embodiment of the present invention will now be described with reference to the drawings.

A. Configuration of the blood pressure monitoring apparatus

FIG. 1 is a block diagram showing an exemplary configuration of the blood pressure monitoring apparatus, which is the embodiment of the present invention. In FIG. 1, a cuff 2 is designed to be attached to a brachium or finger of a subject, and the inside thereof is opened or closed with respect to the atmosphere by an exhaust valve 3. Air is supplied to the cuff 2 by a pressuring pump 4. A pressure sensor 5 is arranged on the cuff main body, and the output of the sensor is detected by a cuff pressure detecting section 6. The output of the cuff pressure detecting section 6 is converted into a digital signal by an A/D converter 7 and is received by a CPU (central processing unit) 1.

A time interval detection reference point detecting section 8 is provided to detect a timing at which the aortic blood pressure reaches a bottom value thereof substantially simultaneously with generation of an ECG R wave. The output of this detecting section 8 is received by the CPU 1 while converted into a digital signal by an A/D converter 9. The time interval detection reference point detecting section 8 can be constructed of electrodes that are attached to the chest of a subject and an ECG R wave detecting section to which the electrodes are connected. It may be noted that the time interval detection reference point detecting section 8 can be constructed also of a photoelectric pulse wave sensor or pressure pulse wave sensor for detecting an aortic pulse wave, and a pulse wave detecting section to which such sensor is connected.

A photoelectric pulse wave sensor 10 is attached to, e.g., a finger of a subject to measure pulse waves at a peripheral blood vessel. When the output of the photoelectric pulse wave sensor 10 is sent to a pulse wave detecting section 11, the pulse wave at the part of the subject to which the sensor is attached can be detected. The output of the pulse wave detecting section 11 is received by the CPU 1 while converted into a digital signal by an A/D converter 12.

Input means 13 inputs an initial pulse wave propagation time change threshold $\Delta Ts$, a blood pressure change threshold $\Delta BPs$, a maximum calibration point count m, and the like. A key 14 is pressed when blood pressure measurement is to be made manually using the cuff 2 and when the pulse wave propagation time change threshold $\Delta Ts$ is to be updated.

The CPU 1 executes a processing program based on signals sent from the A/D converters 7, 9, 12 and the key 14, outputs necessary control signals to the exhaust valve 3, the pressuring pump 4, and the like, and supplies the processed results to a display 15. A ROM 16 that is connected to the CPU 1 has the processing program stored therein. Further, in a RAM 17 are not only data areas arranged for storing blood pressure measurement data but also a counter, a flag, buffers, and registers arranged. Here, the following counter, flag, buffers, and registers are provided.

R$\Delta$Ts: Register for storing a pulse wave propagation time change threshold $\Delta Ts$ R$\Delta$BPs: Register for storing a blood pressure change threshold $\Delta BPs$ Rm: Register for storing a maximum calibration point count m R$\alpha$: Register for storing $\alpha$ R$\beta$: Register for storing $\beta$ RTt: Register for storing a pulse wave propagation time Tt at the current measurement (actually measured value)

RTt$_1$: Register for storing a pulse wave propagation time Tt$_1$ at the current calibration R$\Delta$T: Register for storing a pulse wave propagation time change $\Delta T$ RTc: Register for storing a pulse wave propagation time at the last calibration (actually measured value)

RBPt: Register for storing an actually measured blood pressure value at the current calibration i: Ring buffer address counter k: Flag indicating that the maximum calibration point count has been reached. The flag is set to "1" when the maximum calibration point count has been reached, and "0" in conditions other than this.

BP(i): Ring buffer for storing a measured blood pressure value

T(i): Ring buffer for storing a counted pulse wave propagation time

The cuff 2, the exhaust valve 3, the pressuring pump 4, the pressure sensor 5, the cuff pressure detecting section 6, and the A/D converter 7 constitute the blood pressure measuring means. The RAM 16 corresponds to the blood pressure value storage means, the threshold storage means, and the pulse wave propagation time storage means. The time interval detection reference point detecting section 8 and the A/D converter 9 constitute the time interval detection reference point detecting means. The photoelectric pulse wave sensor 10, the pulse wave detecting section 11, and the A/D converter 12 constitute the pulse wave detecting means. The CPU 1 corresponds to the pulse wave propagation time counting means, the first logic operation means, the second logic operation means, the third logic operation means, the control means, and the judging means.

B. Operation of the blood pressure monitoring apparatus (a) General flowchart

An operation of the thus constructed blood pressure monitoring apparatus will be described next.

Figure 2:
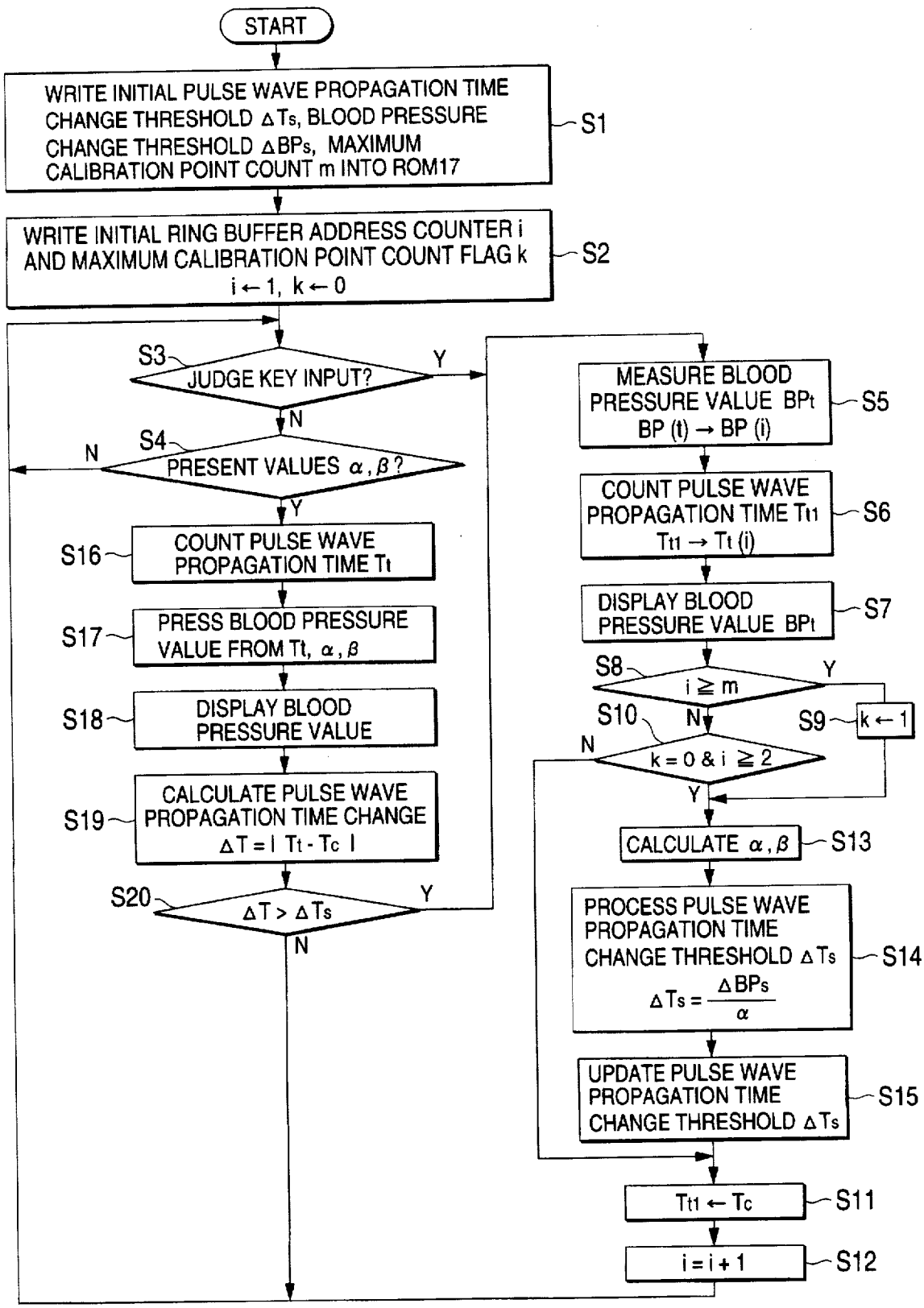
FIG. 2 is a general flowchart showing an operation of the blood pressure monitoring apparatus shown in FIG. 1.

FIG. 2 is a general flowchart showing an operation of the blood pressure monitoring apparatus.

Upon feeding power to the apparatus, an initial pulse wave propagation time change threshold $\Delta Ts$, a blood pressure change threshold $\Delta BPs$, and a maximum calibration point count m are inputted from the input means 13, and these inputted values are stored in the registers R$\Delta$TS, R$\Delta$BPs, Rm in Step S1. Then, in Step S2, the ring buffer address counter i is set to "1", and the maximum calibration point count flag k is reset to "0". Then, in Step S3, it is judged whether or not there is an input through the key 14. If it is judged negatively, then it is judged whether or not the values $\alpha$, $\beta$ are present in Step S4. Since the values $\alpha$, $\beta$ are not present at this point of time, Step S3 will be executed again. If there is no input through the key for an initial blood pressure measurement, Steps S3 and S4 will be executed repetitively.

Under this condition, if the key has been pressed for an initial blood pressure measurement, a blood pressure measurement is made using the cuff 2 in Step S5, and the measured value BPt is written to the ring buffer BP(i) that is specified by the ring buffer address counter i being equal to "1". Then, in Step S6, the pulse wave propagation time Tt$_1$ is counted based on the data from the A/D converters 9, 12, and the measured value is written to the ring buffer T(i) that is specified by the ring buffer address counter i being equal to "1". Then, in Step S7, the blood pressure value BPt already measured and written to the ring buffer BP(1) is displayed on the display 15.

In Step S8, it is judged whether or not the ring buffer address counter i has reached the maximum calibration point count m. If it is judged affirmatively, it means that the ring buffers BP(i) and T(i) are full; i.e., data have been written to all the ring buffers BP(1) to BP(m). Therefore, the maximum calibration point count flag k is set to "1" in Step S9. Since i=1 at this point of time, The processing in Step S9 is not executed, but Step S10 will be executed. In Step S10, it is judged whether or not the maximum calibration point count flag k is set to "0" and the ring buffer address counter i has a count of "2" or more. In this case, since these conditions are not satisfied at this point of time, the pulse wave propagation time Tt$_1$ is written to the register RTc in Step S11. Then in step 12, the ring buffer address counter i is incremented by "1". After this processing in Step S12 has been executed, Step S3 will be executed again to judge whether or not there is an input through the key.

On the other hand, if it is judged in Step S8 that the ring buffer address counter i has reached the maximum calibration point count m, the maximum calibration point count flag k is set to "1" in Step S9, and the processing for calculating the values $\alpha$, $\beta$ is executed in Step S13. This processing is executed based on the blood pressure values and pulse wave propagation times corresponding to the maximum calibration point count. As described above, the values $\alpha$, $\beta$ are the coefficients specific to an individual subject.

Also, when the maximum calibration point count flag k is set to "0" and the ring buffer address counter i has a count of 2 or more in Step S10, the processing for calculating $\alpha$, $\beta$ is executed based on at least two blood pressure values BPt and pulse wave propagation times Tt$_1$ in Step S13.

After the processing for calculating $\alpha$, $\beta$ has been executed, the processing for calculating the pulse wave propagation time change threshold $\Delta Ts$ is executed in Step S14. In this processing, the pulse wave propagation time change threshold $\Delta Ts$ can be obtained by dividing the blood pressure change threshold $\Delta BPs$ by the calculated value $\alpha$. After the pulse wave propagation time change threshold $\Delta Ts$ has been calculated, the pulse wave propagation time change threshold $\Delta Ts$ is written to the register R$\Delta$Ts in Step S15. That is, the pulse wave propagation time change threshold $\Delta Ts$ is updated. After this processing, the pulse wave propagation time Tt$_1$ is written to the register RTc in Step S11, and in step 12, the ring buffer address counter i is incremented by "1". Then, Step S3 will thereafter be executed to judge whether or not there is an input through the key.

As described above, if there is an input through the key for an initial blood pressure measurement, the blood pressure value BPt is measured, and the pulse wave propagation time Tt$_1$ is also counted. As a result, the counted pulse wave propagation time Tt$_1$ is written to the register RTc, and the ring buffer address counter i has a count of "2".

When the initial blood pressure measurement has been made and the values $\alpha$, $\beta$ have therefore been calculated, the pulse wave propagation time Tt is counted based on the data from the A/D converters 9, 12 in Step S16. Then, in Step S17, the processing for calculating the blood pressure value BP from the pulse wave propagation time Tt and the values $\alpha$, $\beta$ is executed. That is, the blood pressure value BP is calculated from P=$\alpha$Tt+$\beta$. Then, the calculated blood pressure value BP is displayed on the display 15 in Step S18. After the processing for displaying the blood pressure value BP has been executed, the processing for calculating the pulse wave propagation time change $\Delta T$ is executed in Step S19. The pulse wave propagation time change $\Delta T$ is calculated from |Tt−Tc|. Then, in Step S20, it is judged whether or not the pulse wave propagation time change $\Delta T$ calculated in Step S19 exceeds the pulse wave propagation time change threshold $\Delta Ts$, i.e., whether or not an inequality $\Delta T>\Delta Ts$ is satisfied. If the inequality $\Delta T>\Delta Ts$ is not satisfied, Step S3 will be executed to repeat a series of processing again. That is, if the pulse wave propagation time change $\Delta T$ does not exceed the pulse wave propagation time change threshold $\Delta Ts$, the processing for counting the pulse wave propagation time Tt is executed consecutively.

In contrast thereto, if it is judged that the inequality $\Delta T > \Delta Ts$ is satisfied in Step S20, it is deemed that there is a sudden change such as a shock in the blood pressure fluctuation of the subject. Therefore, Step S5 will be executed to take care of such a sudden change in the blood pressure fluctuation of the subject; i.e., a blood pressure measurement is made using the cuff 2, and the measured blood pressure value BPt is written to the register RBPt. Further, the pulse wave propagation time $Tt_1$ is counted in Step S6, and the counted value is written to the register $RTt_1$. The measured blood pressure value BPt is displayed on the display 15 in Step S7.

Successively, in Step S8, it is judged whether or not the ring buffer address counter i has reached the maximum calibration point count m. In this case, since the ring buffer address counter i indicates "2", it is judged in Step S10 that the maximum calibration point count flag k is set to "0" and that the ring buffer address counter i has a count of "2" or more. Therefore, the processing for calculating $\alpha$, $\beta$ is executed in Step S13.

After the processing for calculating $\alpha$, $\beta$ has been executed, the processing for calculating the pulse wave propagation time change threshold $\Delta Ts$ is executed in Step S14. Then, in Step S15, the processing for updating the pulse wave propagation time change threshold $\Delta Ts$ is executed. Then, the pulse wave propagation time $Tt_1$ that has been written in the register $RTt_1$ is written to the register RTc. Then in step 12, the ring buffer address counter i is incremented by "1".

As described above, not only the pulse wave propagation time Tt is counted, but also the blood pressure value is calculated from the measured pulse wave propagation time Tt and the values $\alpha$, $\beta$ in the processing from Steps S16 to S19. Such processing from Steps S16 to S19 is executed based on the same $\alpha$, $\beta$ unless the pulse wave propagation time change $\Delta T$ exceeds the pulse wave propagation time change threshold $\Delta Ts$. If the pulse wave propagation time change $\Delta T$ exceeds the pulse wave propagation time change threshold $\Delta Ts$, a blood pressure measurement is made using the cuff 2, so that new $\alpha$, $\beta$ are calculated, and the pulse wave propagation time change threshold $\Delta Ts$ is updated. In this case, if the ring buffer address counter i has not reached the maximum calibration point count m, the values $\alpha$, $\beta$ are calculated based on the blood pressure values and pulse wave propagation times accumulated in the ring buffers up to that point of time. On the other hand, if the ring buffer address counter i has reached the maximum calibration point count m, the values $\alpha$, $\beta$ are calculated based on the blood pressure value and pulse wave propagation time corresponding to such maximum calibration point count.

Here, FIG. 4 is a trend graph showing the measured blood pressure values BPt in function of time and the counted pulse wave propagation times Tt in function of time. As shown in FIG. 4, unless the pulse wave propagation time change $\Delta T$ exceeds the pulse wave propagation time change threshold $\Delta Ts$ after an initial blood pressure measurement has been made using the cuff 2, the pulse wave propagation time Tt is continuously counted. If $\Delta T > \Delta Ts$ at some point of time, then a blood pressure measurement is made using the cuff 2. When the blood pressure measurement has been made using the cuff 2, the ring buffer address counter i has a count of "2", and $\alpha$, $\beta$ are calculated at this point of time. Further, the pulse wave propagation time change threshold $\Delta Ts$ is calculated from the calculated value $\alpha$ and updated.

After the updating operation has been performed, the pulse wave propagation time Tt is consecutively counted. The pulse wave propagation time change threshold $\Delta Ts$ is thereafter updated every time $\Delta T > \Delta Ts$.

(b) The processing for calculating $\alpha$, $\beta$

Figure 3:
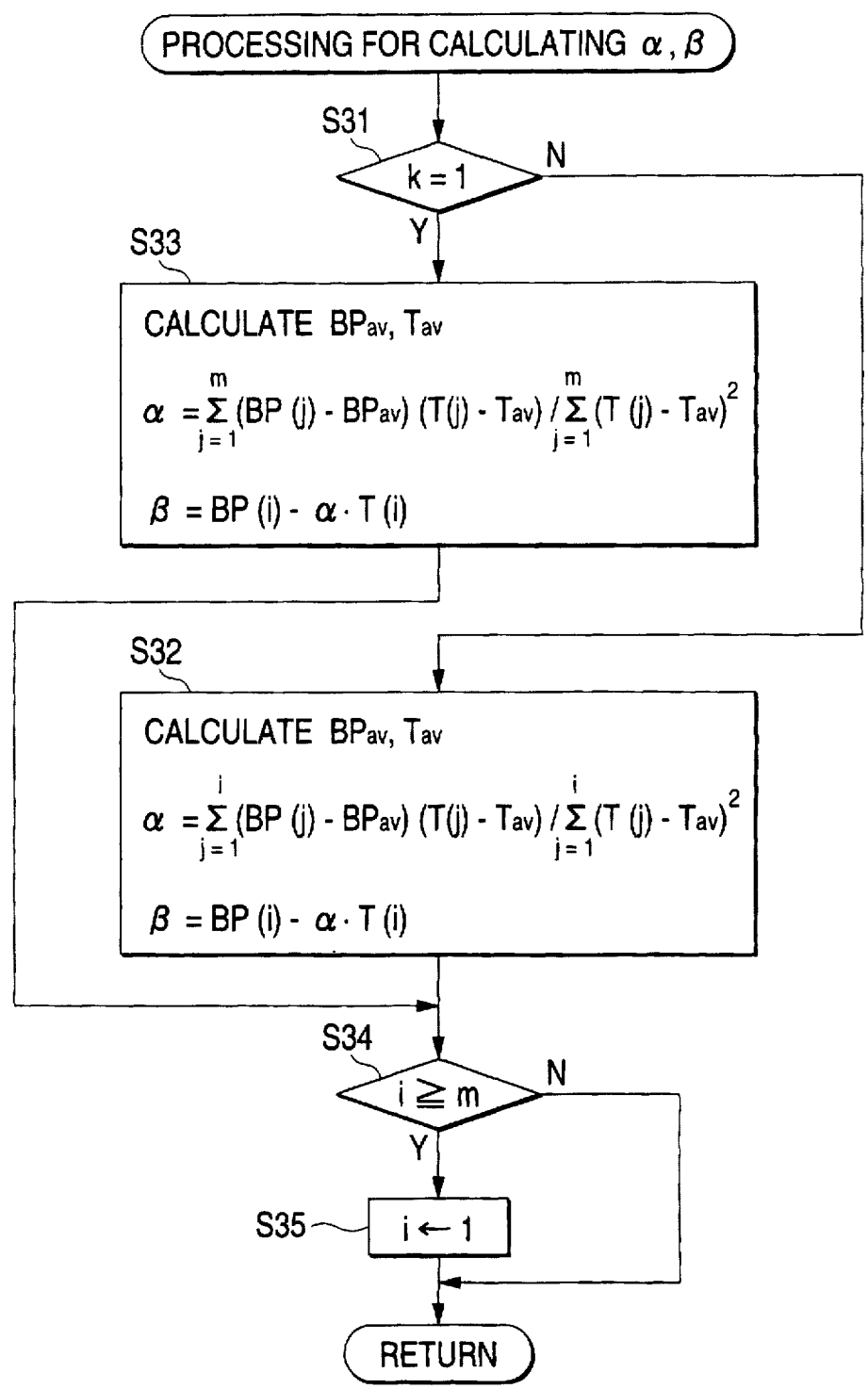
FIG. 3 is a flowchart showing an operation of the blood pressure monitoring apparatus shown in FIG. 1.

FIG. 3 is a flowchart showing the processing for calculating $\alpha$, $\beta$ in the blood pressure monitoring apparatus according to this embodiment. It is judged in Step S31 whether or not the maximum calibration point count flag k is set to "1". If it is judged negatively, i.e., if the number of data pieces of the blood pressure values BPt and pulse wave propagation times $Tt_1$ written to the ring buffers BP(i) and T(i) has not reached the maximum calibration point count m, then $\alpha$, $\beta$ are calculated based on the currently available number of data pieces in Step S32. In this case, $\alpha$, $\beta$ are calculated by the least-squares method. That is, $\alpha$ is obtained by dividing the sum of products of deviatoric of the blood pressure value BPt and deviatoric of the pulse wave propagation time $Tt_1$ by the sum of deviatoric squares of the pulse wave propagation time $Tt_1$, and $\beta$ is obtained by subtracting the product of the average of the pulse wave propagation times $Tt_1$ and $\alpha$ from the average of the blood pressure values BPt.

In Step S32, $\alpha$, $\beta$ are calculated from the blood pressure values BPt and pulse wave propagation times $Tt_1$ corresponding to a value smaller than the maximum calibration point count m, i.e., a count specified by the ring buffer address counter. The value $\alpha$ to be calculated is given as indicated in Eq. 1.

$$\alpha = \frac{\sum_{j=1}^{i} (BP(j) - BP_{av})(T(j) - T_{av})}{\sum_{j=1}^{i} (T(j) - T_{av})^2} \tag{Eq1}$$

In this case, the BPav is an average of the values in the ring buffers BP(1) to BP(i), and the Tav is an average of the values in the ring buffers T(1) to T(i).

On the other hand, $\beta$ is calculated from the following equation.

$$\beta = BP(i) - \alpha \cdot T(i)$$

On the other hand, if it is judged in Step S31 that the maximum calibration point count flag k is set to "1", i.e., the number of data pieces of the blood pressure values BPt and pulse wave propagation times $Tt_1$ written in the ring buffers BP(i) and T(i) has reached the maximum calibration point count m, $\alpha$, $\beta$ are calculated based on the data corresponding to the maximum calibration point count m in Step S33. In this case also, $\alpha$, $\beta$ are calculated by the least-squares method.

In Step S33, $\alpha$, $\beta$ are calculated from the blood pressure values BPt and pulse wave propagation times $Tt_1$ corresponding to the maximum calibration point count m that is a count specified by the ring buffer address counter i. The value $\alpha$ is calculated by an equation indicated in Eq. 2.

$$\alpha = \frac{\sum_{j=1}^{m} (BP(j) - BP_{av})(T(j) - T_{av})}{\sum_{j=1}^{m} (T(j) - T_{av})^2} \tag{Eq2}$$

In this case, the BPav is an average of the values in the ring buffers BP(1) to BP(m), and the Tav is an average of the values in the ring buffers T(1) to T(m).

On the other hand, $\beta$ is calculated from the following equation.

$$\beta = BP(m) - \alpha \cdot T(m)$$

As described above, if there are two or more sets of data, each set of data consisting of a blood pressure value BPt and a pulse wave propagation time $Tt_1$, temporarily stored in the ring buffer BP(i), α, β are calculated by the least-squares method based on such two sets of data.

After the processing in Step S32 or 33 has been completed, it is judged in Step S34 whether or not the ring buffer address counter i indicates a count that is equal to the maximum calibration point count m or more. If it is judged affirmatively, the ring buffer address counter i is set to "1", and the α, β calculating subroutine is terminated. From then on, the values α, β are calculated by the least-squares method for all the data stored in the ring buffers (for m pieces of data). If, on the other hand, the ring buffer address counter i has a count smaller than the maximum calibration point count m, the subroutine is terminated directly.

As described above, in this embodiment, when a command for making an initial blood pressure measurement has been inputted through the key, the blood pressure value BPt is measured with the cuff 2, and the measured blood pressure value BPt is displayed. At the same time, the pulse wave propagation time $Tt_1$ is counted. Immediately thereafter, a measurement of the pulse wave propagation time Tt is started. The pulse wave propagation time Tt is consecutively counted, and the pulse wave propagation time change ΔT is calculated every time the pulse wave propagation time Tt is counted, and the calculated pulse wave propagation time change ΔT is compared with the pulse wave propagation time change threshold ΔTs. When the pulse wave propagation time change ΔT exceeds the pulse wave propagation time change threshold ΔTs, not only the blood pressure value BPt is measured again with the cuff 2, but also the pulse wave propagation time $Tt_1$ is counted again. Further, the values α, β specific to a subject are calculated. Then, the pulse wave propagation time change threshold ΔTs is calculated from the calculated coefficient α, and the current pulse wave propagation time change threshold ΔTs is updated. In this case, the coefficients α, β are calculated based on the least-squares method from at least two sets of data, each set of data consisting of a blood pressure value BPt and a pulse wave propagation time $Tt_1$, which are stored in the past including the blood pressure value BPt and pulse wave propagation time $Tt_1$ currently obtained.

Therefore, by judging whether or not the pulse wave propagation time change ΔT exceeds the pulse wave propagation time change threshold ΔTs while consecutively counting the pulse wave propagation time Tt, not only sudden changes in the blood pressure fluctuation of a subject are monitored, but also a blood pressure measurement is made using the cuff 2 correctly at the time of a sudden change in blood pressure fluctuation, and the pulse wave propagation-time change threshold ΔTs is updated. Therefore, not only burdens given to the subject in the conventional example can be reduced significantly, but also blood pressure fluctuations can be monitored with high accuracy.

It may be noted that pulse wave propagation time counting processing may be made every heart beat or may be made in such a manner that the counting processing is executed at a predetermined time interval or for predetermined heart rates and an average of the counts is then calculated. By calculating the average, accurate pulse wave propagation time counting free from irregularly occurring noise can be implemented.

According to the blood pressure monitoring apparatus of the present invention, a pulse wave propagation time change is calculated every time a pulse wave propagation time is counted consecutively, and the calculated pulse wave propagation time change is compared with a pulse wave propagation time change threshold; if the pulse wave propagation time change exceeds the pulse wave propagation time change threshold, a blood pressure measurement is made using a cuff and a pulse wave propagation time is counted; in this case, if there are at least two sets of data, each set of data consisting of a blood pressure value and a pulse wave propagation time obtained in a blood pressure measurement, including those data stored in the past, coefficients specific to a subject are calculated based on the least-squares method from the respective two sets of data; further, the pulse wave propagation time change threshold is calculated from a calculated coefficient specific to the subject; and the current pulse wave propagation time change threshold is updated. Therefore, it is no longer necessary to measure blood pressure using a cuff at a short cycle as in the conventional example, nor is it necessary to make invasive blood pressure measurements. As a result, burdens given to a subject can be reduced to a significant degree, which in turn allows blood pressure fluctuations to be monitored with high accuracy.

What is claimed is:

1. A blood pressure monitoring apparatus comprising:

blood pressure measuring means for measuring blood pressure using a cuff;

blood pressure value storage means for storing a blood pressure value measured by said blood pressure measuring means;

threshold storage means for storing a pulse wave propagation time change threshold and a blood pressure change threshold that are inputted from external sources;

time interval detection reference point detecting means for detecting a time interval detection reference point on a pulse wave at an aorta of a body;

pulse wave detecting means for detecting a pulse wave at a peripheral blood vessel appearing with a time delay with respect to the pulse wave at the aorta;

pulse wave propagation time counting means for counting a pulse wave propagation time based on detected outputs from said time interval detection reference point detecting means and said pulse wave detecting means;

pulse wave propagation time storage means for storing a pulse wave propagation time counted by said pulse wave propagation time counting means when the blood pressure has been measured by said blood pressure measuring means;

first logic operation means for calculating a pulse wave propagation time change from two pulse wave propagation times counted by said pulse wave propagation time counting means;

second logic operation means for calculating coefficients specific to a subject from at least two blood pressure values stored in said blood pressure value storage means and from the pulse wave propagation times stored in said pulse wave propagation time storage means corresponding to the each blood pressure values, the coefficients allowing equations expressing a relationship between blood pressure and pulse wave propagation time to be established;

third logic operation means for updating a pulse wave propagation time change threshold stored in said threshold storage means by dividing a blood pressure change threshold read from said threshold storage means by a calculated coefficient specific to the subject;

judgement means for judging whether or not the calculated pulse wave propagation time change exceeds the pulse wave propagation time change threshold read from said threshold storage means; and control means for measuring blood pressure of the subject using the cuff by controlling said blood pressure measuring means and controlling the pulse wave propagation time change threshold updating operation when it is judged that the pulse wave propagation time change exceeds the pulse wave propagation time change threshold.

2. A blood pressure monitoring apparatus according to claim 1, wherein the second logic operation means calculates the coefficients specific to the subject by a least-squares method using at least two blood pressure values stored in said blood pressure value storage means and the pulse wave propagation times stored in said pulse wave propagation time storage means corresponding to the two blood pressure values, the coefficients being equivalent to a single regression coefficient and a coefficient term when the relationship between blood pressure and pulse wave propagation time is expressed in the form of a single regression line.

3. A blood pressure monitoring method comprising said steps of:

measuring a blood pressure value using a cuff;

storing said blood pressure value;

storing a pulse wave propagation time change threshold and a blood pressure change threshold that are inputted from external sources;

detecting a time interval detection reference point on a pulse wave at an aorta of a body;

detecting a pulse wave at a peripheral blood vessel appearing with a time delay with respect to the pulse wave at the aorta;

counting a pulse wave propagation time based on detected outputs of the time interval detection reference point and the pulse wave;

storing a pulse wave propagation time counted when the blood pressure has been measured;

calculating a pulse wave propagation time change from two pulse wave propagation times counted;

calculating coefficients specific to a subject from at least two blood pressure values stored and from the pulse wave propagation times stored corresponding to each two blood pressure values, the coefficients allowing equations expressing a relationship between blood pressure and pulse wave propagation time to be established;

updating a pulse wave propagation time change threshold stored by dividing a blood pressure change threshold read by a calculated coefficient specific to the subject;

judging whether or not the calculated pulse wave propagation time change exceeds the pulse wave propagation time change threshold read; and measuring blood pressure of the subject using the cuff by controlling the blood pressure measuring means and controlling the pulse wave propagation time change threshold updating operation when it is judged that the pulse wave propagation time change exceeds the pulse wave propagation time change threshold.

* * * * *